(12) United States Patent
Ryan et al.

(10) Patent No.: US 12,151,035 B2
(45) Date of Patent: Nov. 26, 2024

(54) MULTI STERILIZATION CHAMBER PACK

(71) Applicant: Becton, Dickinson and Company, Franklin Lakes, NJ (US)

(72) Inventors: Kevin M. Ryan, Whitehouse Station, NJ (US); Marco Antonio Ortiz Shields, Summit, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 17/522,505

(22) Filed: Nov. 9, 2021

(65) Prior Publication Data
US 2022/0175979 A1 Jun. 9, 2022

Related U.S. Application Data

(60) Provisional application No. 63/120,988, filed on Dec. 3, 2020.

(51) Int. Cl.
*A61L 2/00* (2006.01)
*B65D 25/04* (2006.01)
*B65D 77/20* (2006.01)

(52) U.S. Cl.
CPC ............ *A61L 2/0005* (2013.01); *B65D 25/04* (2013.01); *B65D 77/2032* (2013.01); *A61L 2202/21* (2013.01); *A61L 2202/23* (2013.01)

(58) Field of Classification Search
CPC ................ A61M 5/002; A61M 25/002; A61M 2209/06; A61M 5/001; A61M 5/3202; A61B 50/30; B65D 77/2032; B65D 75/326; B65D 77/2024; B65D 25/04; B65D 2575/3245

USPC ....... 206/364, 438, 363, 570, 370, 210, 365, 206/571
See application file for complete search history.

(56) References Cited

U.S. PATENT DOCUMENTS 2,834,686 A * 5/1958 Reuman ............... B65D 75/326
 206/525
3,419,137 A * 12/1968 Walck, III .......... B65D 75/5855
 426/123

(Continued)

FOREIGN PATENT DOCUMENTS

CN 106310305 A 1/2017
WO 2012166847 A2 12/2012

(Continued)

OTHER PUBLICATIONS

PCT International Search Report and Written Opinion in PCT/US2021/058897 dated Mar. 3, 2022, 17 pages.

*Primary Examiner* — Steven A. Reynolds
*Assistant Examiner* — Prince Pal
(74) *Attorney, Agent, or Firm* — Servilla Whitney LLC (57) ABSTRACT

A multi-chamber package is described including a first and second chamber, the first chamber having a bottom wall and sidewalls defining a cavity, the second chamber having a partially open bottom wall and sidewalls defining a cavity. A first removable seal is positioned over a top surface of the package, fully covering the first chamber and second chamber, and a second seal is positioned over a bottom surface of the partially open floor of the second chamber, fully sealing the second chamber. A method of packaging medical devices is also described.

17 Claims, 11 Drawing Sheets

(56) References Cited

U.S. PATENT DOCUMENTS

| | | | | |
|---|---|---|---|---|
| 4,106,621 | A | * | 8/1978 | Sorenson ............. B65D 75/328 229/125.35 |
| 4,184,593 | A | * | 1/1980 | Dorr ..................... A61M 5/002 604/227 |
| 4,373,628 | A | * | 2/1983 | Dantes .................. B23Q 13/00 206/349 |
| 4,501,363 | A | * | 2/1985 | Isbey, Jr. ................ A61B 50/33 206/363 |
| 4,522,302 | A | * | 6/1985 | Paikoff ................. A61M 5/003 206/570 |
| 4,722,733 | A | * | 2/1988 | Howson ................ A61J 1/2096 141/330 |
| 4,736,850 | A | * | 4/1988 | Bowman .............. A61F 2/0095 206/370 |
| 4,828,797 | A | * | 5/1989 | Zwarun .................... A61L 2/28 436/1 |
| 4,954,239 | A | * | 9/1990 | Mueller ............... A61M 3/0262 206/278 |
| 5,284,244 | A | * | 2/1994 | O'Toole ................. A61B 50/30 206/467 |
| 5,407,066 | A | * | 4/1995 | Grange .................. A45D 27/29 206/467 |
| 5,407,070 | A | * | 4/1995 | Bascos .................. A61M 5/002 206/467 |
| 5,782,346 | A | * | 7/1998 | Gray ...................... B26B 21/40 30/32 |
| 6,010,462 | A | * | 1/2000 | Stoermer, III ....... B65D 77/245 600/572 |
| 6,220,253 | B1 | * | 4/2001 | Wright ................. A45C 11/008 206/581 |
| 6,311,837 | B1 | * | 11/2001 | Blaustein .............. B65D 75/36 206/362.2 |
| 6,994,213 | B2 | * | 2/2006 | Giard, Jr. ......... A61B 5/150503 206/363 |
| 8,555,900 | B2 | * | 10/2013 | Nicoll .................... B26B 21/44 206/349 |
| 8,727,117 | B2 | * | 5/2014 | Maasarani ............. A61M 5/002 206/364 |
| 8,734,420 | B2 | * | 5/2014 | Ariagno ................ A61J 1/2089 206/370 |
| 9,717,843 | B2 | | 8/2017 | Grucela et al. |
| 10,029,043 | B2 | | 7/2018 | Grucela et al. |
| 10,080,813 | B2 | | 9/2018 | Felder et al. |
| 2001/0025865 | A1 | * | 10/2001 | Bravo .................. B65D 23/108 222/561 |
| 2001/0032799 | A1 | * | 10/2001 | Shinada ............... B41J 2/17553 206/576 |
| 2002/0108875 | A1 | * | 8/2002 | Feinberg .......... A61B 17/00491 206/364 |
| 2002/0185406 | A1 | * | 12/2002 | Massengale ........... A61B 50/30 206/570 |
| 2003/0196922 | A1 | * | 10/2003 | Reaux ................... A61B 50/20 206/370 |
| 2005/0211595 | A1 | * | 9/2005 | Hull ....................... A61B 50/30 206/363 |
| 2006/0096877 | A1 | * | 5/2006 | Khajavi ............. A61B 50/3001 206/363 |
| 2006/0283749 | A1 | * | 12/2006 | Wolfe .................... B65D 75/36 359/623 |
| 2008/0125721 | A1 | * | 5/2008 | Timm ..................... A61P 27/06 220/500 |
| 2009/0149527 | A1 | * | 6/2009 | Timm .................. A61K 31/407 206/572 |
| 2009/0200198 | A1 | * | 8/2009 | Guelzow ............ B65D 81/3261 422/4 |
| 2009/0321292 | A1 | * | 12/2009 | Prudden, Jr. ............. B65D 1/30 53/412 |
| 2010/0181218 | A1 | * | 7/2010 | Beccaro ................ A61F 9/0017 604/218 |
| 2010/0200443 | A1 | * | 8/2010 | Greene .................. B65D 25/10 206/372 |
| 2011/0127188 | A1 | * | 6/2011 | Thompson ............... B32B 27/08 206/524.6 |
| 2011/0139647 | A1 | * | 6/2011 | Petricca ............... A45D 27/225 53/485 |
| 2011/0284410 | A1 | * | 11/2011 | Lockwood ......... B65D 21/0202 206/364 |
| 2012/0145589 | A1 | * | 6/2012 | Macinnes .............. A61B 50/30 53/411 |
| 2013/0299364 | A1 | * | 11/2013 | Kobbe .................. B65D 5/4204 206/15.2 |
| 2014/0013718 | A1 | * | 1/2014 | Maasarani ......... B65D 77/2032 206/364 |
| 2014/0231295 | A1 | * | 8/2014 | Ponzini ................ B65D 75/366 53/471 |
| 2014/0353190 | A1 | * | 12/2014 | Okihara ................. B65B 55/10 206/370 |
| 2015/0021221 | A1 | * | 1/2015 | Hendrickson .......... A61B 50/20 206/438 |
| 2015/0182686 | A1 | * | 7/2015 | Okihara ............. B65D 79/0084 206/365 |
| 2016/0022361 | A1 | * | 1/2016 | Khajavi ................. G16H 20/40 705/2 |
| 2016/0136049 | A1 | * | 5/2016 | Weinstein .............. B65D 25/04 206/570 |
| 2016/0228676 | A1 | * | 8/2016 | Glithero ............... A61M 25/002 |
| 2018/0161490 | A1 | | 6/2018 | Sanders et al. |
| 2018/0161491 | A1 | | 6/2018 | Sanders et al. |
| 2018/0296749 | A1 | | 10/2018 | Grucela et al. |
| 2019/0307911 | A1 | * | 10/2019 | Bala ........................ A61L 2/208 |
| 2020/0338259 | A1 | * | 10/2020 | Mainz .................... A61B 50/30 |
| 2021/0378776 | A1 | * | 12/2021 | Yoshida ................. A61B 50/30 |
| 2022/0133426 | A1 | * | 5/2022 | O'Flynn ............. B65D 73/0078 206/210 |
| 2022/0133981 | A1 | * | 5/2022 | Dumont ............ A61M 5/31505 206/364 |
| 2023/0248898 | A1 | * | 8/2023 | Cook ..................... A61M 5/002 604/500 |
| 2023/0413975 | A1 | * | 12/2023 | Holley ................. B65D 75/366 |

FOREIGN PATENT DOCUMENTS

| | | |
|---|---|---|
| WO | 2015122964 A1 | 8/2015 |
| WO | 2019199636 A2 | 10/2019 |

* cited by examiner

MULTI STERILIZATION CHAMBER PACK

CROSS-REFERENCE TO RELATED APPLICATIONS

This application claims priority under 35 U.S.C. § 119(e) to U.S. Provisional Application No. 63/120,988, filed Dec. 3, 2020, the disclosures of which are incorporated herein by reference in their entirety.

TECHNICAL FIELD

The present invention relates to multi-chamber packages, and more particularly to multi-chamber packages requiring different sterilization processes.

BACKGROUND

Clean or sterile articles particularly useful for medical applications are packaged to preserve their sterility. The packaging for these articles is intended to provide a barrier to prevent microorganisms from entering inside the packaging to contaminate its contents. In most instances, the packaging is opened immediately prior to using the article, such as with a package housing a syringe, so as to minimize the time period in which the article is exposed to unsterile conditions.

In medical industries, articles placed in packaging often need to be sterilized during the packaging process and different sterilization methods can be used for different articles. Conventionally, sterilized articles are placed in separate packages from non-sterilized articles. Furthermore, articles conventional packages are packaged at the same time in a single enclosed package. Alternatively, a sterilized article is placed in an individual package and subsequently placed in a non-sterilized kit package. These configurations and methods create more packaging waste and require more steps to unpack the kit.

Many medical procedures require multiple components including medication and medical devices which must be collected by the clinician prior to beginning the procedure. The practice of assembling multiple components in advance of a procedure is known as "kitting" and many hospitals and independent companies provide a service by assembling these components and preparing them for use in medical procedures. In many instances, the multiple components including medication and medical devices require different sterilization processes.

For example, drugs or other injectable/infusible solutions which are packaged in gas-permeable containers such as plastic ampoules, drug vials with rubber stoppers, IV solution bags, IV solution pouches and pre-filled flush syringes are commonly used in medical procedures and may be included in procedure kits. In many instances, the plastic ampoules, drug vials with rubber stoppers, IV solution bags, IV solution pouches and pre-filled syringe contains saline and other aqueous solutions. Ethylene oxide (EtO) sterilization is common methods used to prepare the kit for use in a sterile field. Currently, pre-filled saline syringes, plastic ampoules, drug vials with rubber stoppers, IV solution bags, IV solution pouches are packaged in gas permeable packaging which is also permeable to EtO gas, which is commonly used for sterilization of medical instruments. However, exposure of a plastic ampoules, drug vials with rubber stoppers, IV solution bags, IV solution pouches or pre-filled syringe to Ethylene Oxide (EtO) gas results in an undesirable effect of increasing the pH of the contents of the plastic ampoules, drug vials with rubber stoppers, IV solution bags, IV solution pouches or pre-filled syringe, e.g. saline. To overcome this undesired effect, the plastic ampoules, drug vials with rubber stoppers, IV solution bags, IV solution pouches or plastic pre-filled saline syringe is initially omitted from the medical procedure kit until after the other contents of the kit have been treated with Ethylene Oxide (EtO) gas. For some medical procedures, it is important to have sterile field ready plastic ampoules, drug vials with rubber stoppers, IV solution bags, IV solution pouches and/or pre-filled flush syringe which also could be sterilized following the assembly of the kit. Thus, there is a need for packaging that can accommodate products that requires different sterilization methods packaged, for example, pre-filled flush syringe, plastic ampoules, drug vials with rubber stoppers, IV solution bags, IV solution pouches that are capable of withstanding EtO sterilization.

Conventional packaging consumes a significant amount of material as a kit of multiple articles may require multiple packages. This extra packaging material leads to an increase in the cost of each syringe product. Moreover, the additional packaging then needs to be discarded upon opening the package, leading to an increase in the amount of waste material produced in a hospital or other medical setting.

There is an increasing need for kit packs that contain product that requires different sterilization methods for sterile and non-sterile products. Thus, there is a need for packaging that can accommodate products that requires different sterilization methods for sterile and non-sterile products.

SUMMARY

Aspects of the invention are directed to a package housing a medical product, including devices, prefilled syringes or medication.

One aspect of the present disclosure pertains to a package container having a package body including a top surface and a bottom surface, a first chamber protruding from the bottom surface of the body having sidewalls and a closed chamber floor, a first cavity including the top surface of the body, the sidewalls of the first chamber and the closed chamber floor of the first chamber, and a second chamber protruding from the bottom surface of the body having sidewalls and an at least partially open chamber floor, the top surface of the body. The second cavity comprising the sidewalls of the second chamber and the at least partially open chamber floor. A first removable webbing is disposed over the top surface of the body and a second removable webbing disposed over the at least partially open chamber floor.

In one or more embodiments, a first device is positioned within the first cavity and a second device is positioned within the second cavity.

In one or more embodiments, the first removable webbing is has a peel tab.

In one or more embodiments, the first removable webbing is peelable.

In one or more embodiments, the second removable webbing is not peelable.

In one or more embodiments, the cavity of the first chamber has a length slightly larger or equal to the total length of a first device, a width slightly larger or equal to the maximum width of the first device a depth slightly larger or equal to the maximum depth of the first device.

In one or more embodiments, the cavity of the second chamber has a length slightly larger or equal to the total length of a second device, a width slightly larger or equal to the maximum width of the second device and a depth slightly larger or equal to a maximum depth of the second device.

Another aspect of the present disclosure pertains to a method of packaging medical devices including positioning a first medical device in a first cavity of a package body, sterilizing the first medical device and the first cavity with a first sterilization process, sealing the first cavity by positioning a first removable webbing over a top surface of the package body, positioning a second medical device in a second cavity of the package body, and, sealing the second cavity by positioning a second removable webbing over an at least partially open chamber floor of the second cavity.

In one or more embodiments, the method further includes sterilizing the second medical device and the second cavity with a second sterilization process. In one or more embodiments, the first sterilization process and second sterilization process are the same. In one or more embodiments, the first sterilization process is different from the second sterilization process.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

With respect to terms used in this disclosure, the following definitions are provided.

As used herein, the terms "package" or "packaging" includes any material used to wrap or protect a medical device or product, such as plastic ampoules, drug vials with rubber stoppers, IV solution bags, IV solution pouches and syringes. Packaging can be rigid or flexible. Packaging includes, but is not limited to, medical packaging, pharmaceutical packaging, and child-resistant packaging. Medical and pharmaceutical packaging can include plastic trays with webbing, blister packs, flow wrap and 3 or 4 sided pouches.

As used herein, the terms "blister package" or "blister pack" includes several types of pre-formed packaging used for consumer goods, pharmaceuticals, medical devices, etc. The primary component of a blister pack is a cavity or pocket made from a formable web, usually a thermoformed plastic. The formable web can be rigid or flexible. The cavity or pocket is large enough to contain the good which is housed in the blister package. Depending on the application, a blister pack may have a backing of thermoformable material and a lidding seal of aluminum foil, paper, Tyvek®, plastic, or other medical grade materials. Blister packages can provide barrier protection from microorganisms and other contaminants, and can provide a certain degree of tamper resistance. The blister pack protects the pharmaceutical product from outside influences that would otherwise render it useless while allowing the manufacturer of the pharmaceutical product to package it using form-fill-seal equipment. The form-fill-seal process involves creating the blister pack from rolls of flat sheet or film, filling with the medical device or pharmaceutical product.

The lidding film of a medical blister pack can be made from plastic, aluminum, or medical grade papers that are permeable to gases for sterilization but are impermeable to microorganisms. Most commonly, Tyvek® is used as a lidding material for medical blister packs.

Blister packs can be sealed in a variety of ways including, but not limited to, heat-sealing and cold sealing. Lidding materials can have a heat-seal coating applied to them; the lidding is then sealed to the backing using heat, which activates the coating. Blister packs can also be sealed using a cold seal process, which uses a combination of a pressure sensitive fold-over blister card and a transparent blister; the blister is trapped between two pieces of board that are bonded together under pressure without using any heat. Additionally, blister packs can be sealed by orienting multiple layers of film properly in order to make a seal.

Tyvek® is a synthetic material consisting of flashspun high-density polyethylene fibers (i.e. a spunbound olefin fiber). The material is lightweight and strong, and is resistant to tearing but can be cut with scissors or a knife. Water vapor and other gases can pass through Tyvek® as the material is highly breathable, but, at the same time, the material is impermeable to liquid water and microorganisms.

Reference to "syringe" includes syringes that are indicated for use with needles, nozzle, tubing, or for use in flush systems. As used herein, the term "syringe" refers to a simple pump-like device consisting of a plunger rod that fits tightly in a barrel or tube. The plunger rod can be pulled or pushed along inside the barrel, allowing the syringe to take in and expel a liquid or gas through an opening at the open end of the barrel. The open end of the syringe may be fitted with a needle, nozzle, or tubing to help direct the flow of fluid into and out of the barrel. The syringe may be sterile or unsterile, depending upon the needs of the technician.

As used herein, the term "sterilization" refers to a wide variety of techniques employed to attenuate, kill or eliminate harmful or infectious agents. Examples of sterilization procedures include, for example, steam sterilization, ethylene oxide sterilization, gas plasma sterilization, ozone sterilization, hydrogen peroxide sterilization, heat sterilization, nitrous dioxide sterilization, or a combination thereof.

As used herein, the term "gas permeable" is intended to mean a material which will allow gas to pass through the material but does not allow airborne microbes, bacteria, viruses and mixtures thereof to pass through the material.

As used herein, "gas impermeable" is intended to mean a material which does not readily allow gas to pass through the material. In addition, the gas impermeable material also fails to allow airborne microbes, bacteria, viruses and mixtures thereof to pass through the material.

As used herein, the term "microorganism" refers to a microbe or organism that is unicellular or lives in a colony of cellular organisms. Microorganisms are very diverse; they include, but are not limited to bacteria, fungi, archaea, and protozoans.

During manufacturing, pre-filled medical devices are placed in a gas-impermeable section or chamber of a package and is sterilized with non-toxic or hazardous sterilization processes such as a steam sterilization in an autoclave. The sterilized gas-impermeable section or chamber of a package is then fully sealed. In one or more embodiments, sterilization may also be by heat, nitrous dioxide, or a combination thereof. Because the pre-filled medical device is fully enclosed in pouch consisting only of gas-impermeable film, the pouch containing the pre-filled medical device may be place in a kit that will undergo subsequent EtO sterilization without any adverse effects to the pre-filled medical device. As such, excess steps and excess materials are used in the formation of a kit.

A first aspect of the present invention relates to a package container having two or more chambers, each of the two or more chambers having an article disposed within the two or more chambers. A first removable seal is positioned over a top opening of the two or more chambers, fully sealing a first of the two or more chambers and a second seal is positioned over a bottom opening of a second of the two or more chambers, sealing the second chamber. A second aspect of the present invention relates to a method of packaging two or more articles, the method comprising the steps of positioning a first article in a first chamber, positioning a first removable seal over a top opening of the two or more chambers, thereby sealing the first chamber, positioning a second article in the second chamber, positioning a second removable seal over a bottom opening of the second chamber, thereby sealing the second chamber.

Figure 1:
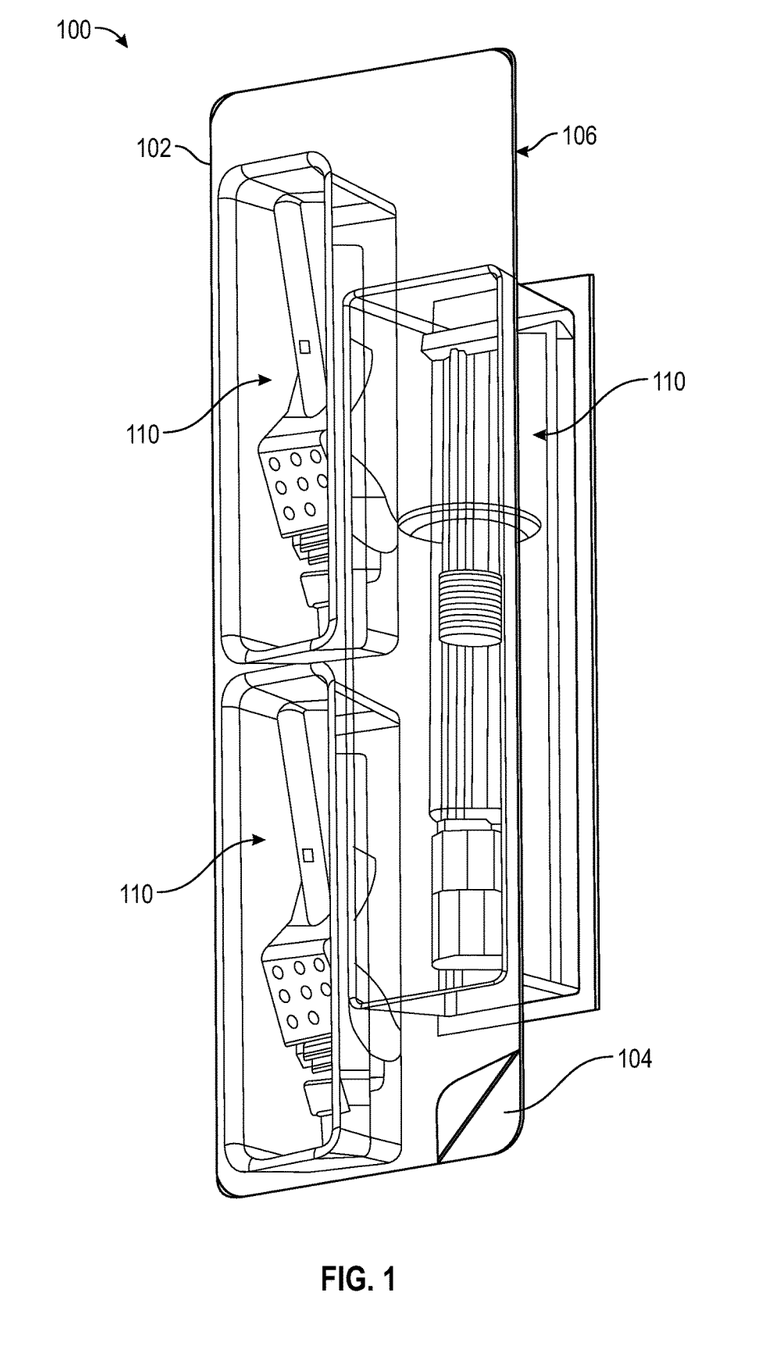
FIG. 1 illustrates a perspective view of a package container in accordance with an embodiment of the present disclosure.

FIG. 1 illustrates a package container 100 in accordance with one or more embodiments of the present disclosure. For illustrative purposes, the package container 100 is depicted as translucent. The package container 100 comprises a package body 102 having a top surface 104 and a bottom surface 106 defining a thickness. From the bottom surface extend two or more chambers 110. Each of the two or more chambers 110 have a bottom and walls defining a cavity. Disposed within the cavities of each of the one or more chambers 110 are articles for packaging.

In some embodiments, the package container 100 is a blister package. In some embodiments, the package container 100 is hard plastic. In some embodiments, package container 100 is a soft plastic. In some embodiments, the package container 100 is glass, ceramic, metal or a metal alloy. In some embodiments, the package container 100 is translucent to allow a practitioner to see the contents of the two or more chambers 110. In some embodiments, the package container 100 is opaque. In some embodiments, the package container 100 has symbols or markings indicating the date of manufacture, the contents within or warning labels.

Figure 2A:
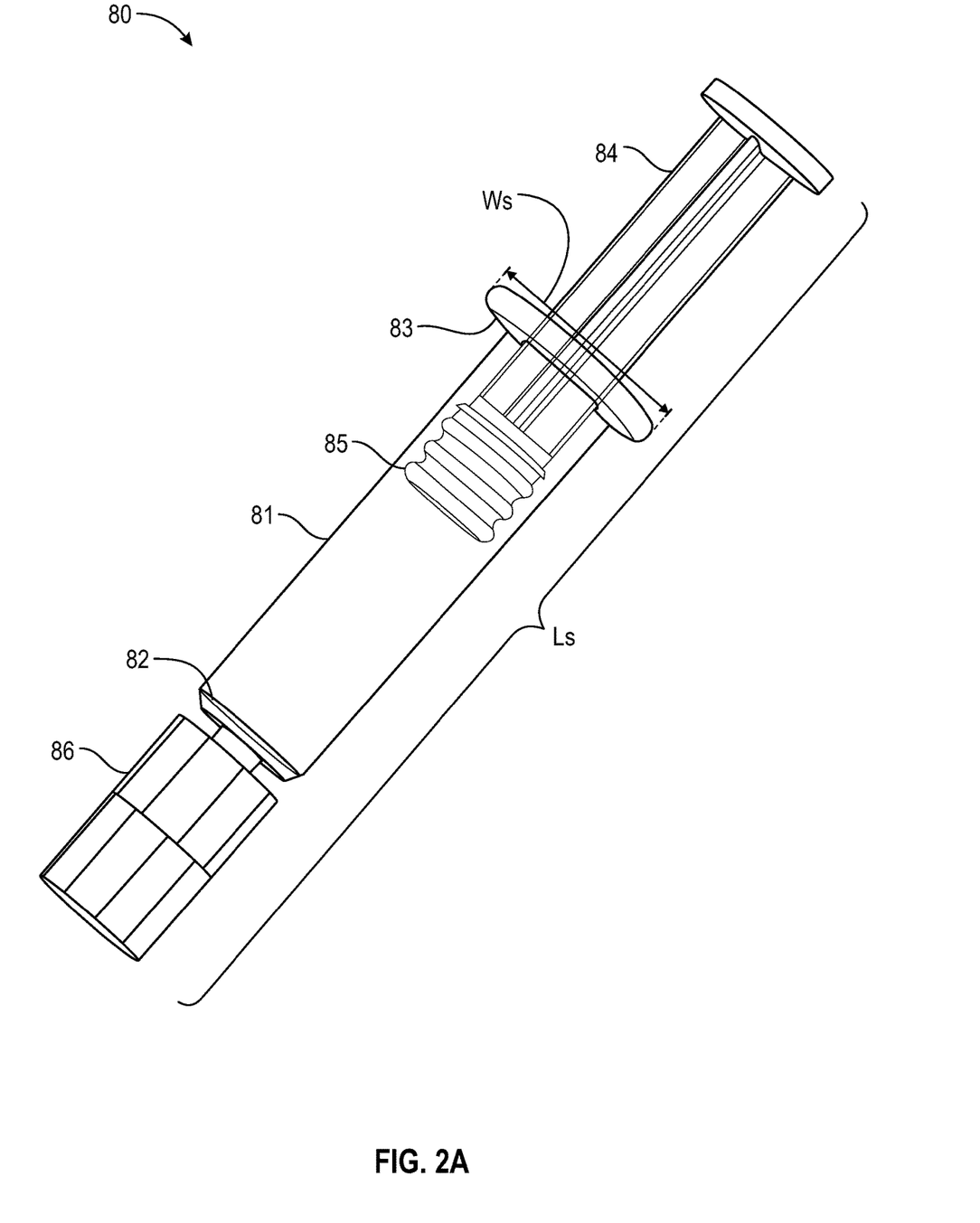
FIG. 2A illustrates a perspective conventional syringe in accordance with one or more embodiments of the present disclosure.
Figure 2B:
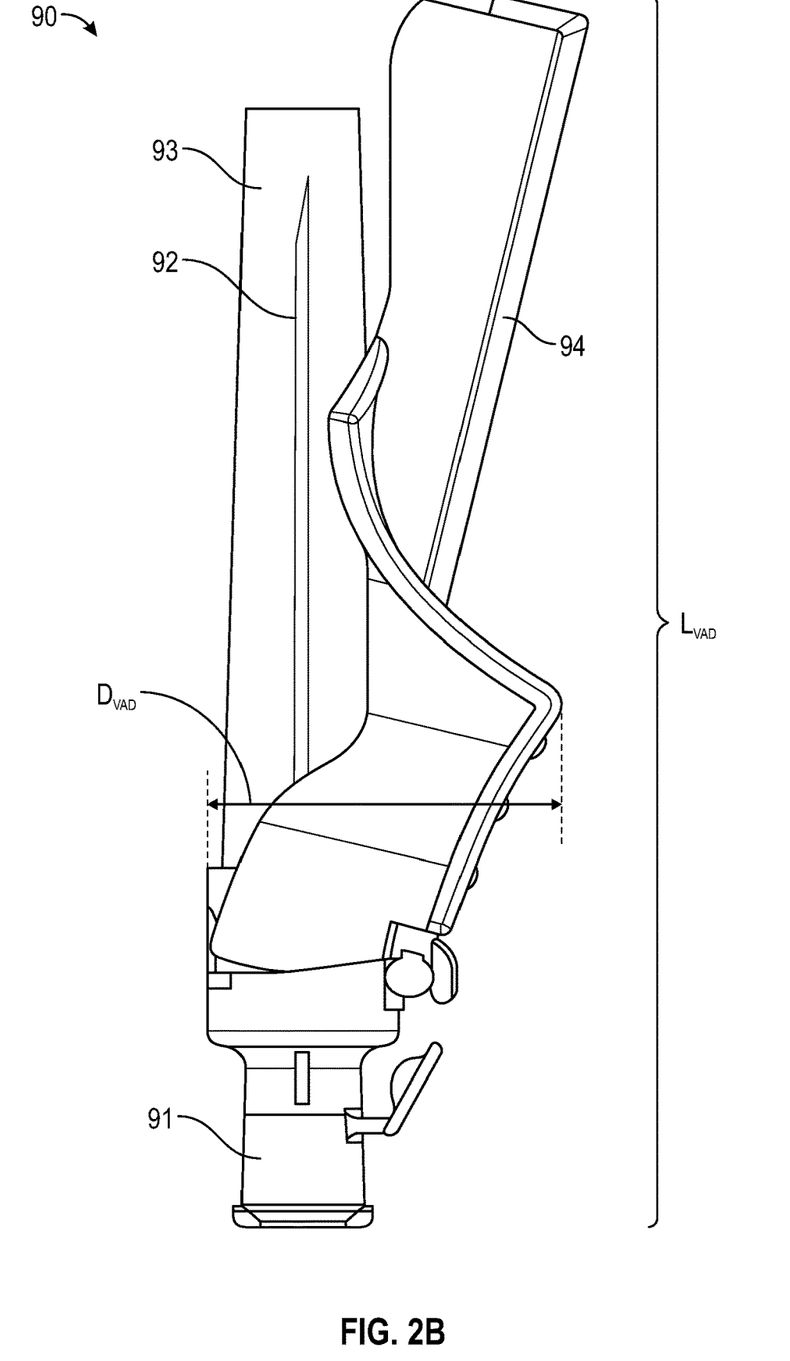
FIG. 2B illustrates a front view of a conventional vascular access device in accordance with one or more embodiments of the present disclosure.

FIGS. 2A and 2B illustrate conventional medical devices which, in one or more embodiments, are articles disposed within the package container 100. The described conventional medical devices are not intended to be limiting examples, as articles which are disposed in the package container 100 can be any device. The described conventional medical devices occupy a volume defined in the XYZ plane. The X-plane, Y-plane and Z-plane are at right angles to one another. The corresponding volumes of each of the two or more chambers 110 are configured to be equal to or slightly larger than the volumes of the articles. In some embodiments utilizing blister packaging, the volumes of the two or more chambers 110 conform to the shape of the articles. The volumes of each of the two or more chambers 110 can be any suitable shape. In some embodiments, the shape of the two or more chambers 110 is trapezoidal, trigonal oval, or rectangular.

FIG. 2A illustrates a conventional syringe 80. The syringe 80 comprises a barrel 81 having a closed distal end 82 and an open proximal end 83. From the closed distal end 82 extends a needleless connector. A plunger rod 84 having a distally located stopper 85 is at least partially disposed within the barrel 81. In some embodiments, the syringe 80 is a pre-filled flush syringe. In some embodiments, the syringe 80 is packaged with a vascular access device attached to the needless connector. In some embodiments, the syringe 80 is packaged with a cap 86. As illustrated in FIG. 2A, the syringe 80, inclusive of all components of the syringe 80, has a total length Ls in a Z-plane and a maximum width Ws in a X-plane, the maximum width Ws measured at the widest portion of the syringe 80 transverse to the total length Ls. In the present embodiment, the total length Ls extends from the barrel 81 to the cap 86 and the maximum width Ws is defined by a flange of the open proximal end 83. In the present embodiment, the flange is substantially cylindrical in shape and has a constant maximum width Ws defined by a diameter of the flange of the open proximal end 83. In some embodiments, the open proximal end 83 comprises two tabs, and thus the syringe 80 has a maximum width Ws and a depth in a Y-plane.

Figure 2C:
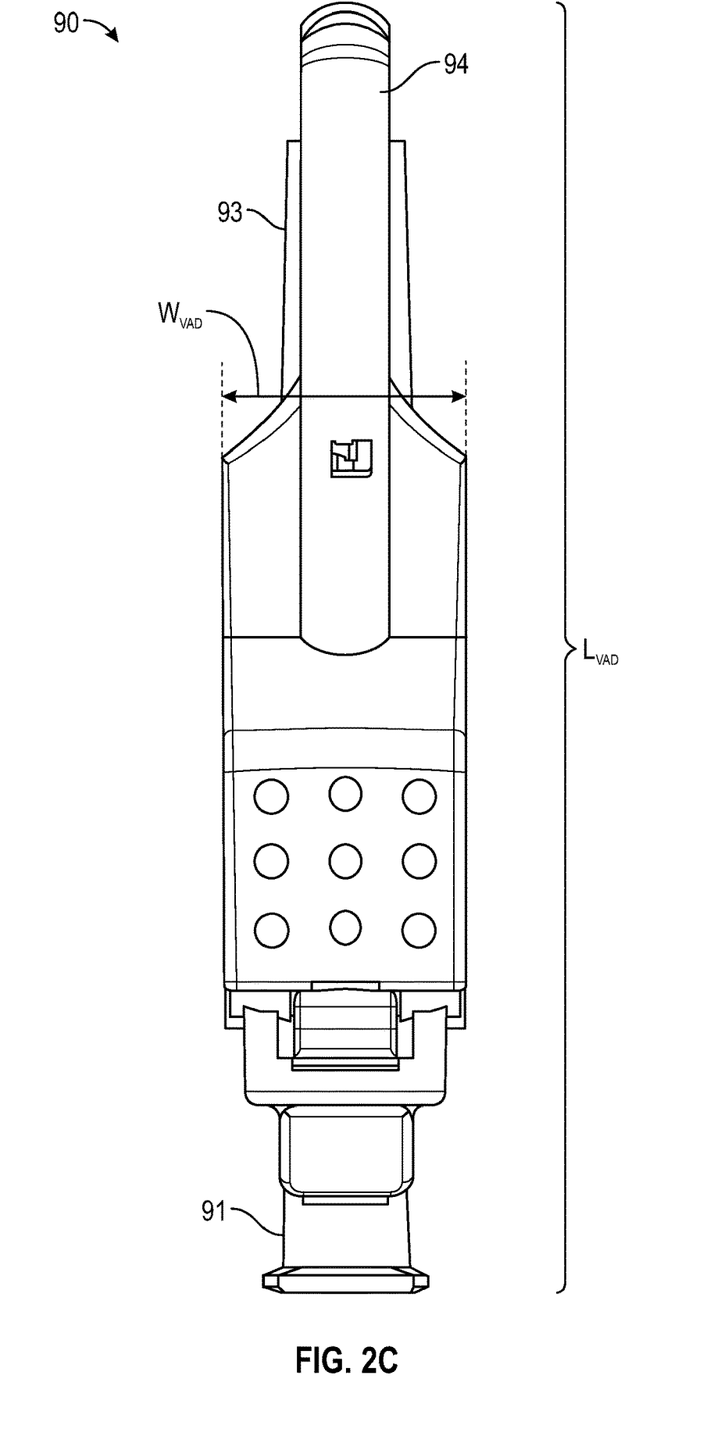
FIG. 2C illustrates a side view of a conventional vascular access device in accordance with one or more embodiments of the present disclosure.

FIGS. 2B and 2C illustrate a conventional vascular access device 90. The vascular access device 90 comprises a hub 91 housing a needle 92. In some embodiments, the vascular access device 90 further comprises a needle cap 93 and a hinged safety cover 94. As illustrated in FIGS. 2B and 2C, the vascular access device 90, inclusive of all components of the vascular access device 90, has a total length $L_{VAD}$ in a Z-plane, a maximum width $W_{VAD}$ in an X-plane, the maximum width $W_{VAD}$ measured at the widest portion of the vascular access device 90 transverse to the total length $L_{VAD}$ and a maximum depth $D_{VAD}$, the maximum depth $D_{VAD}$ measured at the widest portion of the vascular access device 90 transverse to the total length $L_{VAD}$.

In the present embodiment, the total length $L_{VAD}$ extends from the hub 91 to the hinged safety cover 94. The maximum width $W_{VAD}$ is defined by a width of the hinged safety cover 94. The maximum depth is $D_{VAD}$ is defined by a distance from the hub 91 to the hinged safety cover 94.

Figure 3:
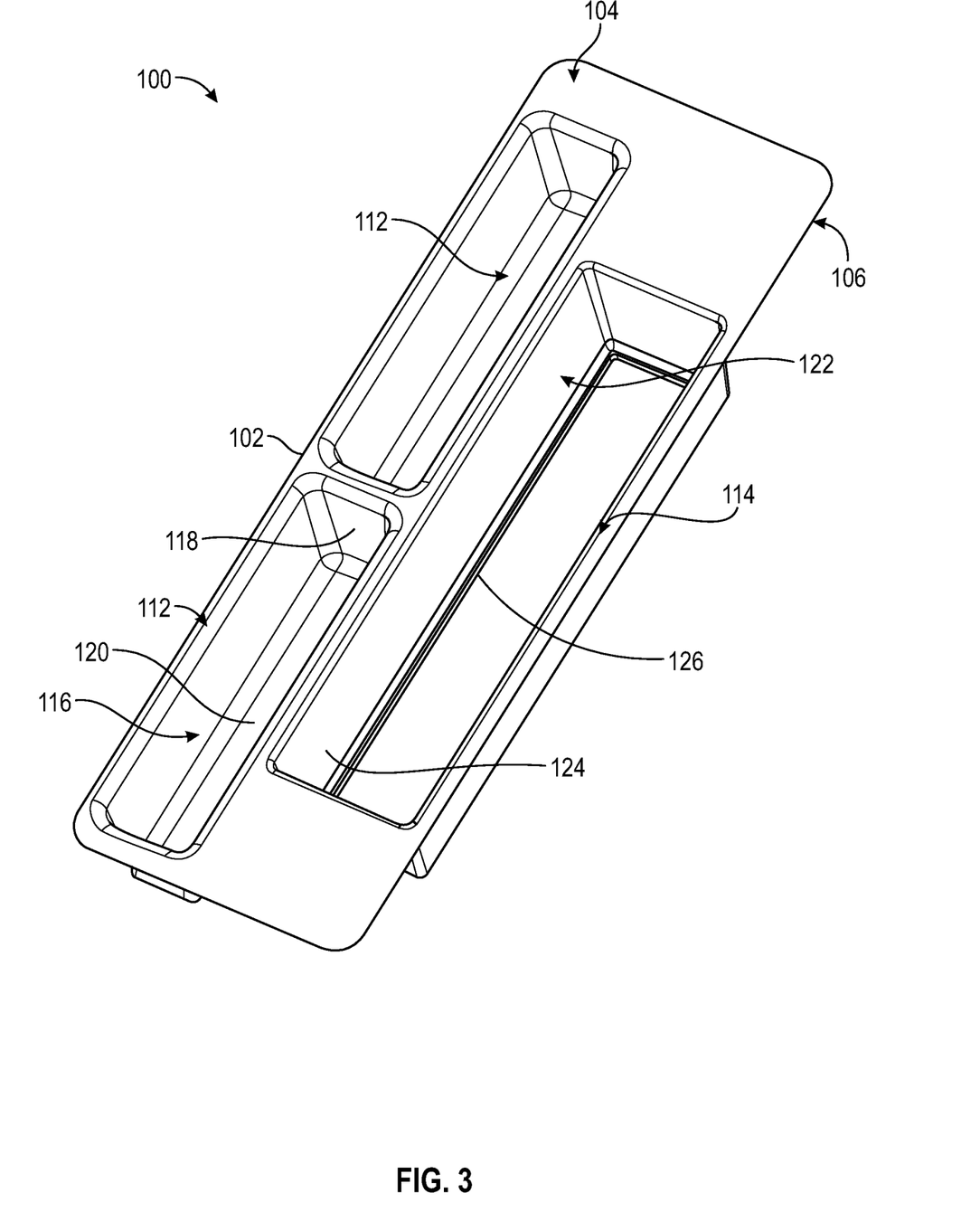
FIG. 3 illustrates a top perspective view of a package container in accordance with an embodiment of the present disclosure.

FIG. 3 illustrates the package container comprising a package body 102 having a top surface 104 and a bottom surface 106 defining a thickness. From the bottom surface extend two or more chambers. The two or more chambers are sized and shaped to house a single article, multiple articles or multiple articles as a kit or assembly. In the present embodiment as illustrated in FIG. 3, a first chamber 112 of the two or more chambers is sized to hold the vascular access device 90 (of FIG. 2B and a second chamber 114 is sized to hold the syringe 80 (of FIG. 2A). In one or more embodiments, there are two first chambers 112 for holding two vascular access devices 90.

The first chamber 112 has a cavity 116 defined by sidewalls 118 and a closed chamber floor 120. The cavity 116 has a rectangular shape and is configured to hold the vascular access device 90. To accommodate the vascular access device 90, the cavity 116 has a length slightly larger or equal to the total length $L_{VAD}$ of the vascular access device 90. Likewise, the cavity 116 has a width slightly larger or equal to the maximum width WVAD of the vascular access device 90 and a depth slightly larger or equal to the maximum depth $D_{VAD}$ of the vascular access device 90.

The second chamber 114 has a cavity 122 defined by sidewalls 124 and an at least partially open chamber floor 126. The cavity 122 has a rectangular shape and is configured to hold the syringe 80. To accommodate the syringe 80, the cavity 122 has a length slightly larger or equal to the total length Ls of the syringe 80. Likewise, the cavity 122 has a width slightly larger or equal to the maximum width Ws of the syringe 80 and a depth slightly larger or equal to the maximum depth Ds of the syringe 80. In some embodiments, the at least partially open chamber floor 126 forms a lip 128 and a bottom surface 130 (as shown in FIG. 5B).

Figure 4:
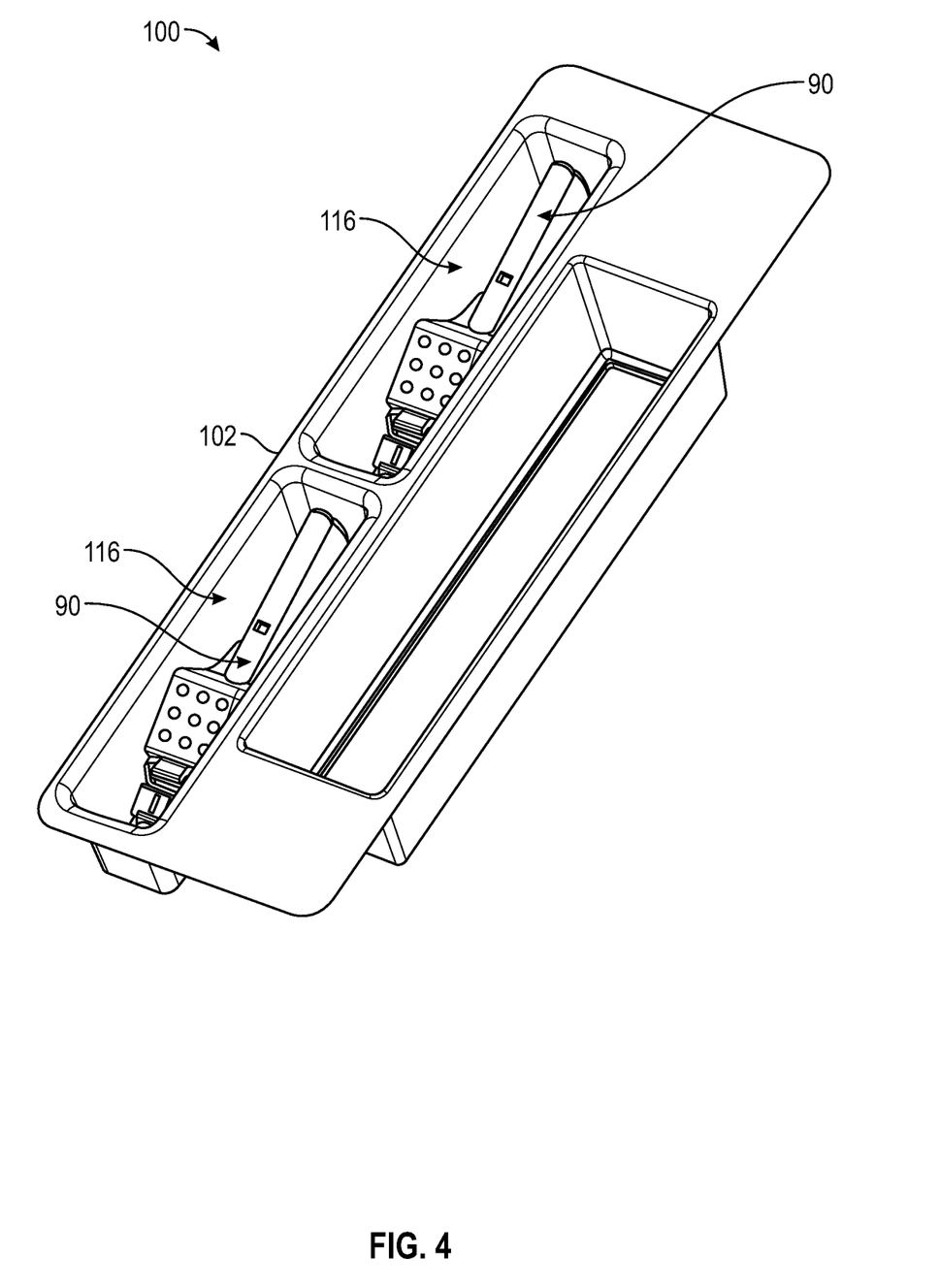
FIG. 4 illustrates a top perspective view of a package container in accordance with an embodiment of the present disclosure.

As shown in FIG. 4, vascular access devices 90 are positioned within the cavity 116 of the first chamber 112. As shown in the present embodiment, there are two first chambers 112 each having a vascular access device 90 positioned within.

Figure 5A:
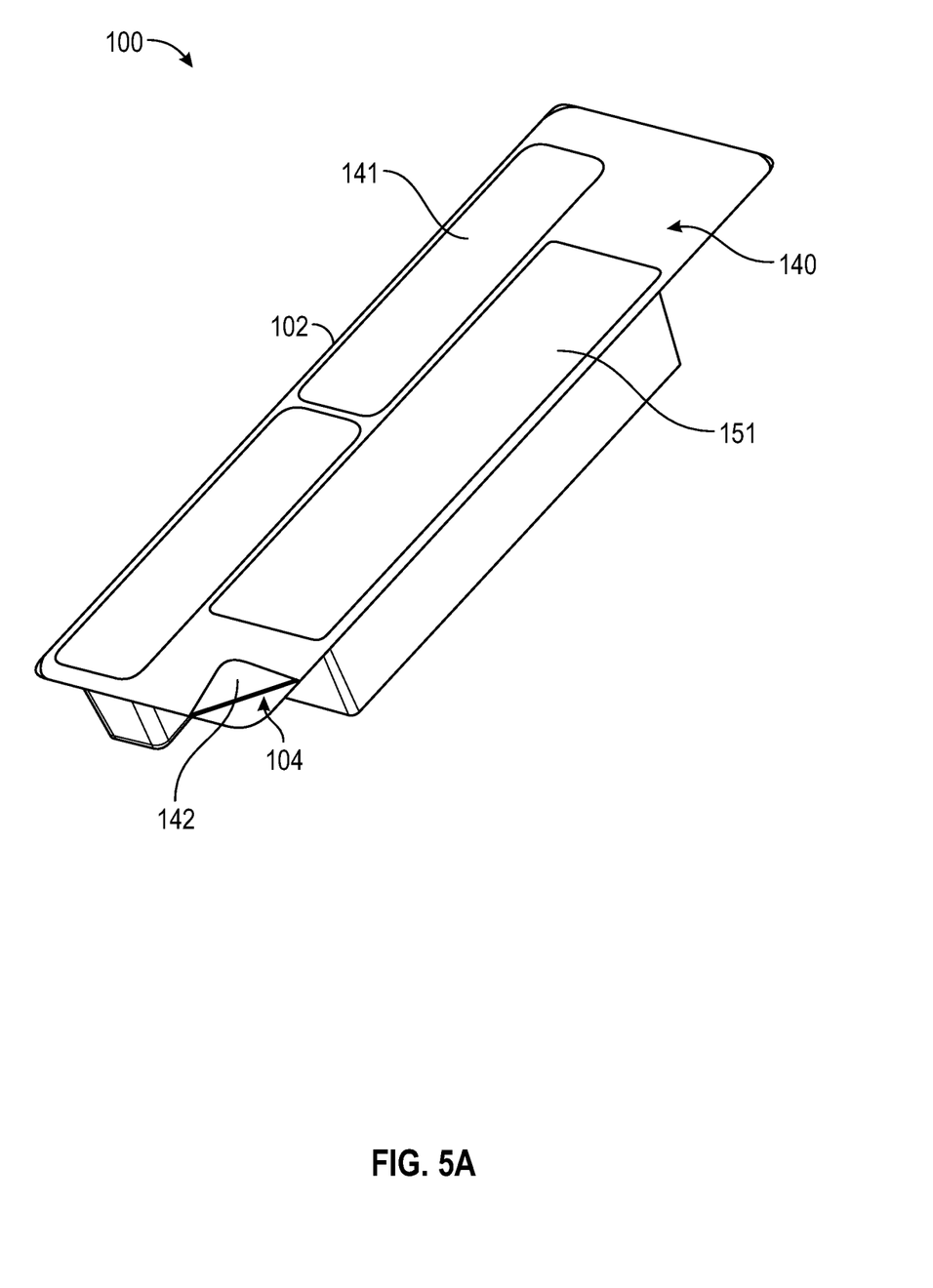
FIG. 5A illustrates a top perspective view of a package container in accordance with an embodiment of the present disclosure.
Figure 5B:
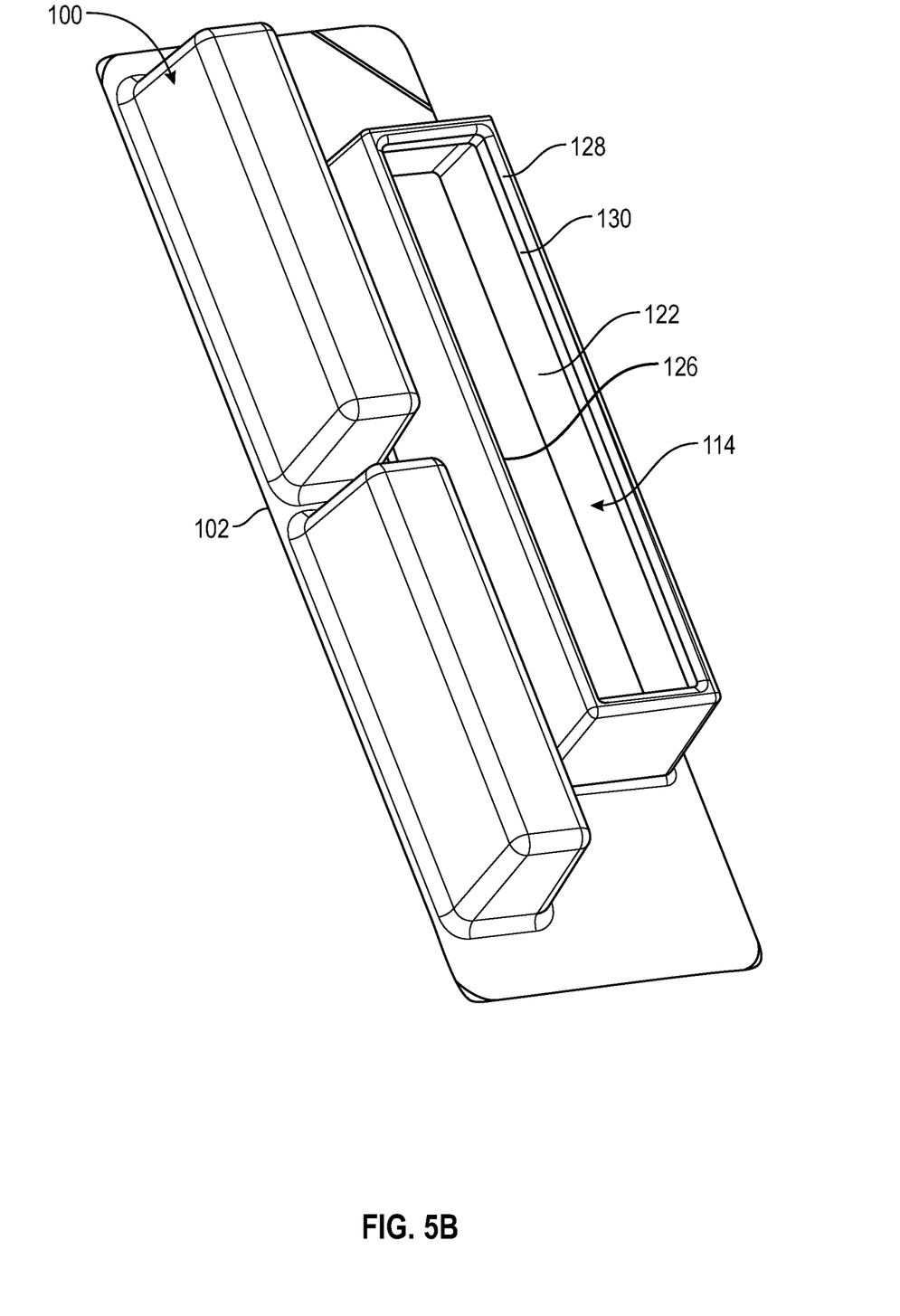
FIG. 5B illustrates a bottom perspective view of a package container in accordance with an embodiment of the present disclosure.

As shown in FIG. 5A, a first removable webbing 140 is positioned over the top surface 104, completely covering and sealing the first chamber 112 and second chamber 114 in a gas-impermeable section. In some embodiments, the first removable webbing 140 has a peel tab 142. As shown in FIG. 5B, due to the second chamber 114 having an at least partially open chamber floor 126, the cavity 122 of the second chamber 114 is exposed even after the first removable webbing 140 is applied to the top surface 104 of the package body 102 in order to sterilize the contents of the second chamber 114 without affecting the contents of the first chamber 112.

Figure 6:
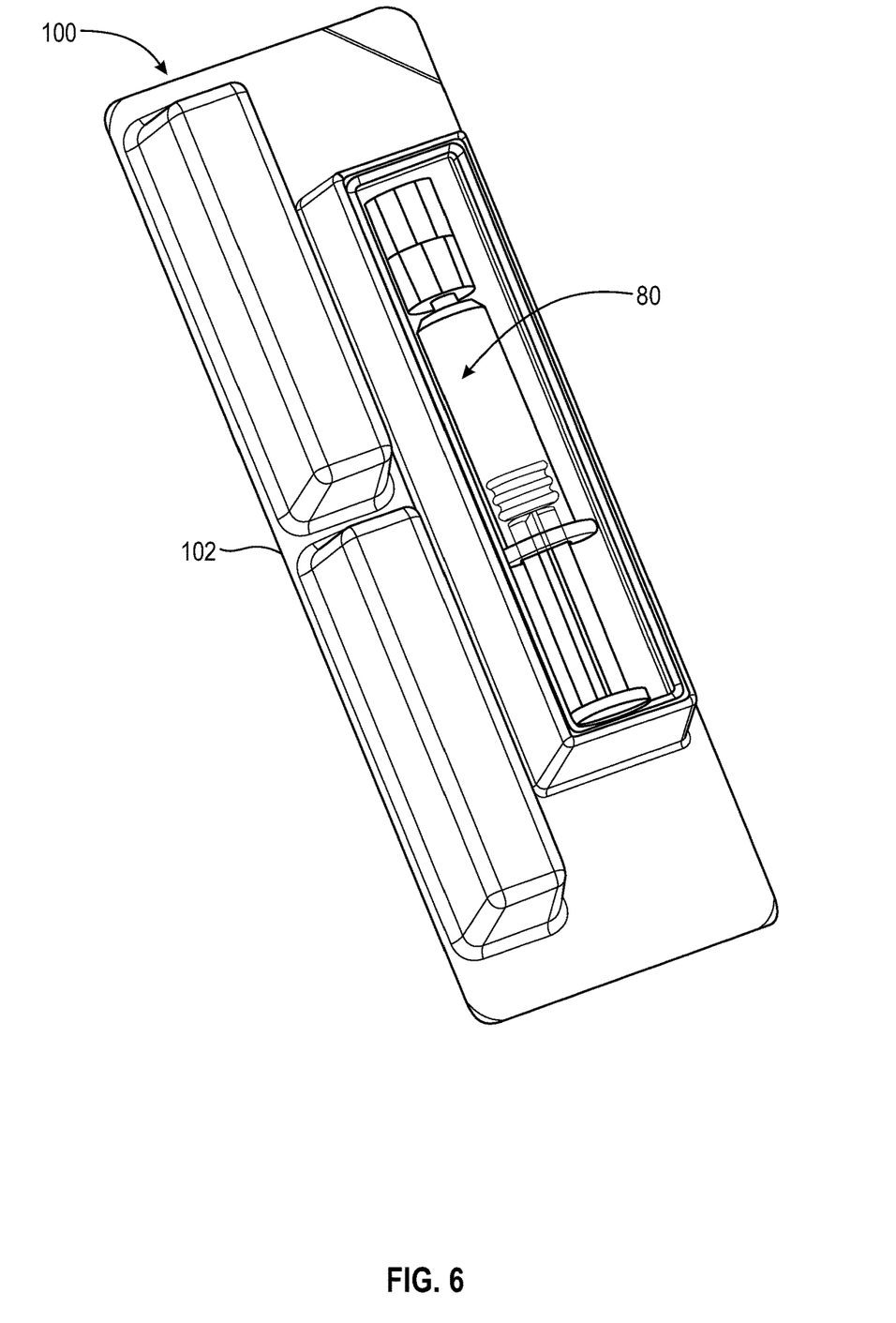
FIG. 6 illustrates a bottom perspective view of a package container in accordance with an embodiment of the present disclosure.
Figure 7:
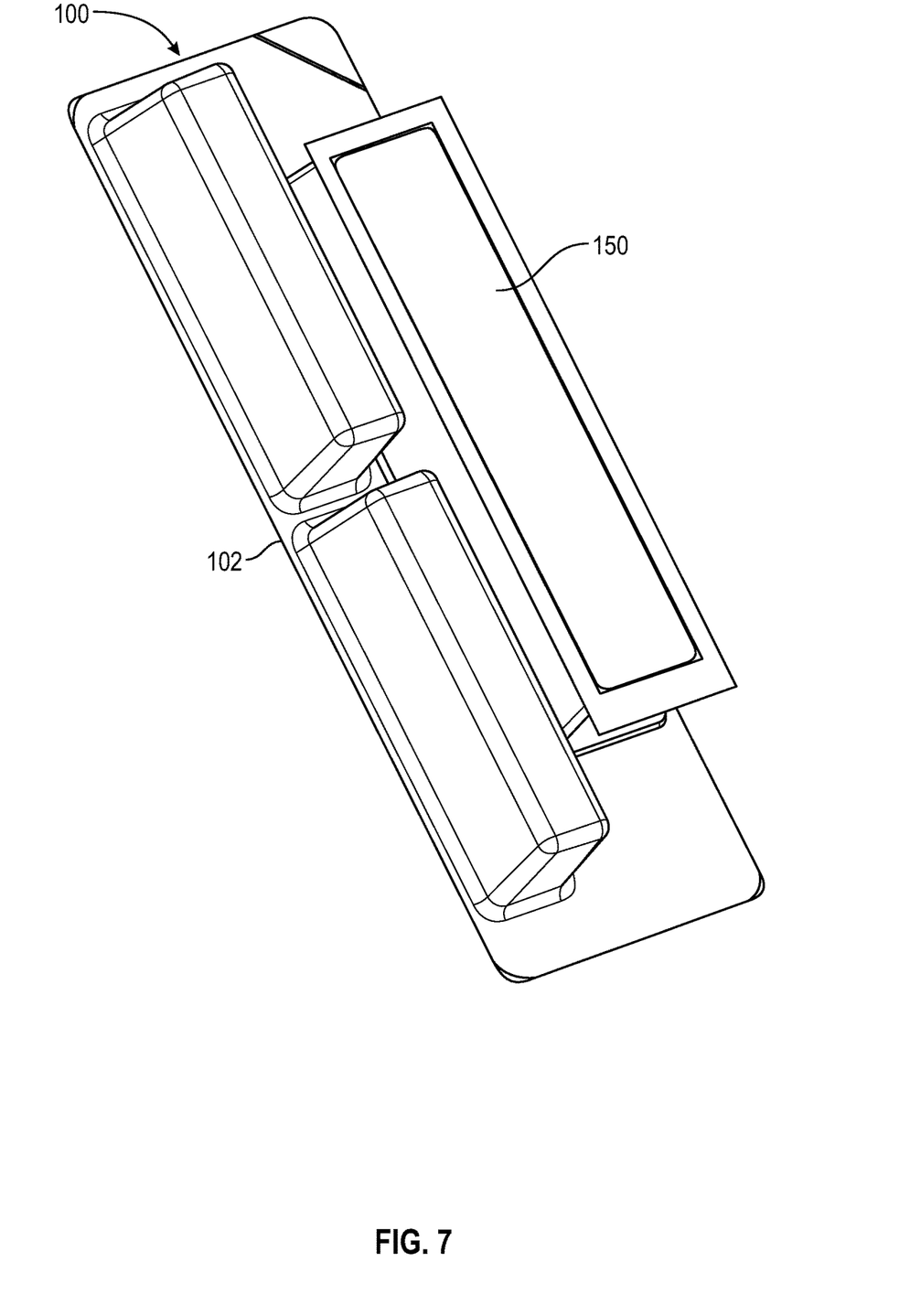
FIG. 7 illustrates a bottom perspective view of a package container in accordance with an embodiment of the present disclosure; and, FIG. 8 illustrates a flowchart of a method of packaging one or more devices container in accordance with an embodiment of the present disclosure.

As shown in FIGS. 6 and 7, the syringe 80 can be placed within the cavity 122 of the second chamber 114. The bottom surface 130 of the second chamber 114 can then be covered by a second removable webbing 150.

In some embodiments, one or more of the first removable webbing 140 and second removable webbing 150 include a gas permeable section attached to a separate gas impermeable section, which allows for sterilization using steam, heat, nitrous dioxide, or a combination thereof through the gas permeable section. Upon sterilization, the gas permeable section of some embodiments can be sealed or removed, creating a chamber which is gas impermeable. In some embodiments, an outer periphery of one or more of the first removable webbing 140 and second removable webbing 150 is the gas permeable section and an inner region surrounded by the outer periphery is the gas-impermeable section. In some embodiments, the entire first removable webbing 140 is gas impermeable. In some embodiments, the entire first removable webbing 140 is gas permeable. In some embodiments, the entire second removable webbing 150 is gas impermeable. In some embodiments, the entire second removable webbing 150 is gas permeable. In some embodiments, as best shown in FIG. 5A, only areas directly above the first chamber 112 and second chamber 114 are gas impermeable or gas permeable. Specifically, a surface area 141 of the first removable webbing 140 directly above the first chamber 112 and/or a surface area 151 of the first removable webbing 140 above the second chamber 114 are gas impermeable or gas permeable. Selection of gas-impermeable or gas permeable areas or webbings are dependent upon the contents within the first chamber 112 or second chamber 114. The gas permeable section can be disposed at any location on the packaging that enables the method of sterilization.

By having the first chamber 112 completely sealed by the first removable webbing 140 and the second chamber 114 subsequently fully sealed by the second removable webbing 150, the package container 100 enables the packaging of a first article separate from the packaging of a second article without exposing the second article to the sterilization procedures or methods of sealing the first chamber 112 with the first removable webbing 140. By way of example, flush syringes, medical devices having rubber stoppers or vials containing medical fluid can be adversely affected by certain chemicals or methods of sterilization, such as ETO sterilization. By placing these sensitive medical devices in the first chamber 112 only, a sterilization can be performed on these sensitive medical devices. The first chamber 112 can then be sealed by the first removable webbing 140, and then other medical devices which are not sensitive to certain chemicals or methods of sterilization, such as ETO sterilization, can be placed in the second chamber 114, sterilized and subsequently sealed by the second removable webbing 150. Thus, a kit is created utilizing less steps than conventional means as previously described. Said benefit can be applied to one or more embodiments of the present disclosure, including the method 200 discussed in detail below.

Another aspect of the present disclosure pertains to a method 200 of packaging medical devices including positioning a first medical device in a first cavity of a package body, sterilizing the first medical device and the first cavity with a first sterilization process, sealing the first cavity by positioning a first removable webbing over a top surface of the package body, positioning a second medical device in a second cavity of the package body, and, sealing the second cavity by positioning a second removable webbing over an at least partially open chamber floor of the second cavity.

In one or more embodiments, the method includes only one sterilization process. In one or more embodiments, the method includes sterilizing the first medical device and the first cavity with a first sterilization process. In one or more embodiments, the method further includes sterilizing the second medical device and the second cavity with a second sterilization process. In one or more embodiments, the first sterilization process and second sterilization process are the same. In one or more embodiments, the first sterilization process is different from the second sterilization process. In one or more embodiments, the first sterilization process utilizes sterilization methods and chemicals which are non-toxic or do not adversely affect sensitive medical devices, such as steam or UV light. Thus, in one or more embodiments, the first sterilization process utilizes sterilization methods and chemicals which do not include ETO sterilization. In one or more embodiments, the second sterilization process utilizes ETO sterilization.

Figure 8:
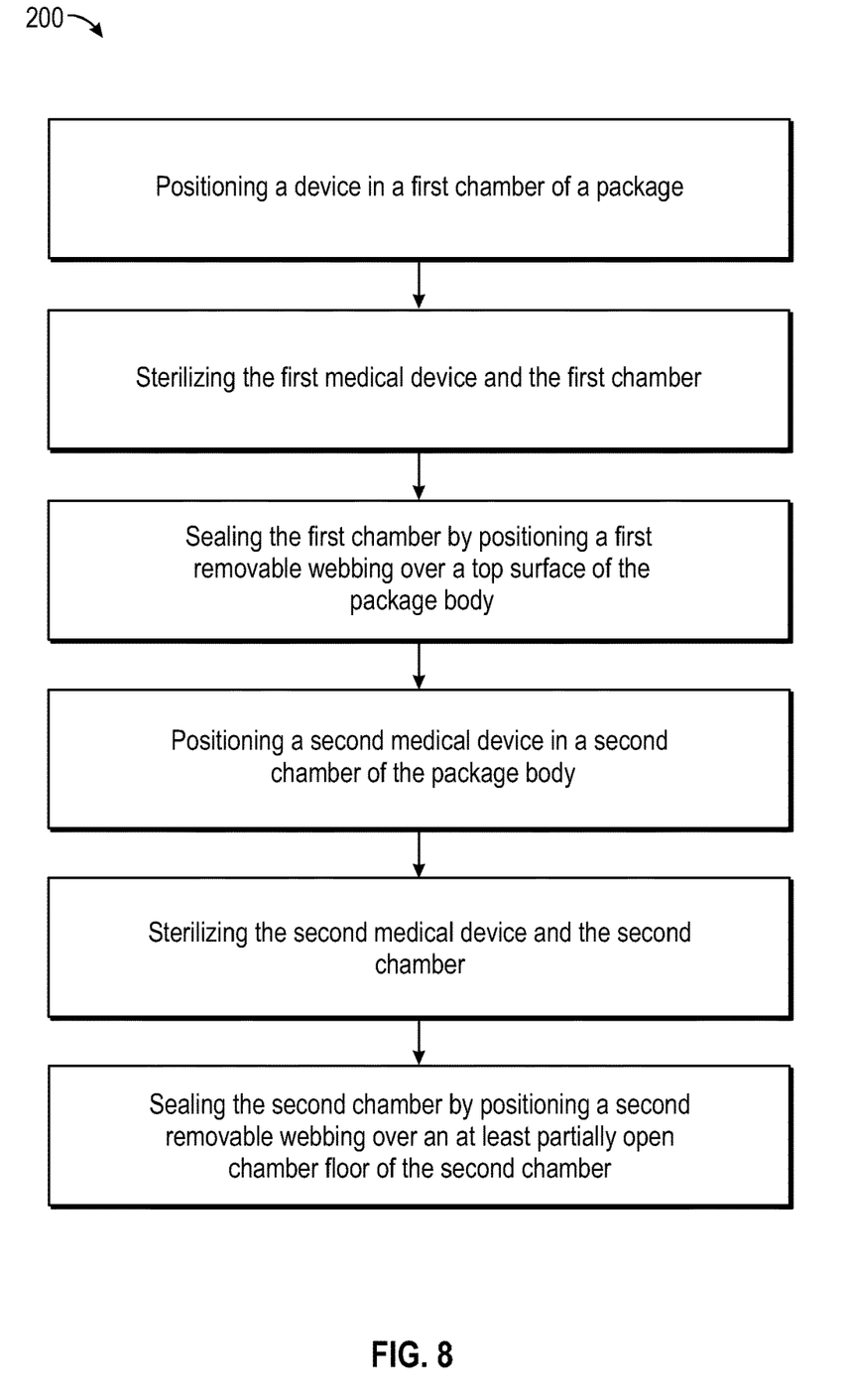

FIG. 8 illustrates a flow chart for an exemplary method of packaging medical devices, the method comprising the steps of positioning a first device or an article in the first chamber 112 and sterilizing the first device and the first chamber 112. The steps further comprise sealing the first chamber 112 and the second chamber 114 by positioning the first removable webbing 140 over the top surface 104 of the package body 102. The steps further comprise positioning a second medical device in the second chamber 114, sterilizing the second medical device and the second chamber 114 and sealing the second medical device and the second chamber 114 by positioning the second removable webbing 150 over the bottom surface 130 of the second chamber 114.

In the method described, in some embodiments, the first medical device or article is the conventional vascular access device 90 and the second medical device or article is the syringe 80. In some embodiments, the sterilization practice of the first chamber 112 differs from the sterilization practice of the second chamber 114. In some embodiments, the first chamber 112 is sealed by positioning the first removable webbing 140 over the top surface 104 of the package body 102 but is not sterilized. In some embodiments, the second chamber 114 is sealed by positioning the second removable webbing 150 over the bottom surface 130 of the second chamber 114 but is not sterilized.

In some embodiments, the method further comprises sterilizing the first chamber 112 with steam sterilization in an autoclave. In one or more embodiments, sterilization may also be by heat, nitrous dioxide, or a combination thereof. Following sterilization, the first removable webbing 140 is applied to the top surface 104 of the package body 102. Following application of the first removable webbing 140, and because the syringe has not yet been positioned within the second chamber 114, the entire package 100 may undergo subsequent EtO sterilization without any adverse effects to the syringe. The syringe is positioned in the second chamber 114 and the second removable webbing 150 is applied, fully enclosing the syringe. In some embodiments, both the first removable webbing 140 and the second removable webbing 150 is gas-impermeable, the entire package 100 can undergo EtO sterilization without any adverse effects to the syringe In some embodiments, the peel tab 142 is for allowing the technician to use when opening the package to release the article disposed within the first or second chamber.

In some embodiments, the first removable webbing 140 and the second removable webbing 150 are plastic films such as flexible thermoformable plastics, including, but not limited to, nylon based films with polyethylene and ethyl vinyl acetate (EVA). The first removable webbing 140 and the second removable webbing 150 can comprise Tyvek® or other medical grade materials such as paper or flexible films. The flexible web backing materials are permeable to radiation and to gas, but are not permeable to microorganisms. Thus, the packages according to one or more embodiments can be sterilized.

In some embodiments, the articles disposed within the chambers (namely the syringe 80 and the vascular access device 90 of the present embodiments) can be squeezed out of the package with one hand, thereby penetrating the first removable webbing 140 and the second removable webbing 150. In some embodiment, the holding force of the first removable webbing 140 and second removable webbing 150 will vary depending upon the type of article contained within the chambers. Larger or heavier syringes are likely to require a higher/larger holding force than smaller or lighter syringes In some embodiments, the first removable webbing 140 is peelable. In some embodiments, the second removable webbing 150 is ultrasonically or heat welded. In some embodiments, the second removable webbing 150 is of the same material as the first removable webbing 140. In some embodiments, the second removable webbing 150 is semi permeable film. In some embodiments, the second removable webbing 150 is not peelable.

It should be understood that the size and location of the gas permeable membrane or section is not limited to any particular configuration and that the position and size can be selected to meet the particular requirements of the end user. Additionally, it should be understood that the size and position of the first and second chambers is not limited to any particular configuration and can vary depending on the articles stored within. Additionally, the position and size of the gas permeable membrane can be selected to optimize the sterilization process. In the figures, the first removable webbing 140 and second removable webbing 150 is depicted as having a single gas permeable membrane having a generally rectangular shape. However, it should be recognized that the present invention is not limited to any particular number, shape or size of the first removable webbing 140 and second removable webbing 150 the first removable webbing 140 and second removable webbing 150 can include multiple gas permeable membranes of varying shapes and sizes.

In one or more embodiments, the type of packaging 100 may be blister, flow wrap, 3 or 4 sided seal pouch.

In one or more embodiments, the present invention can be applied on either blister packaging or flow wrap packaging equipment for automated manufacturing.

In one or more embodiments, the material for the first removable webbing 140 and second removable webbing 150 or a section of the first removable webbing 140 and second removable webbing 150 may be paper or Tyvek which are able to survive the autoclave process.

In accordance with one aspect of the present invention, a desiccant, an antioxidant, an oxygen scavenger, an oxygen barrier or a combination thereof may be added to one or more of the first chamber or second chamber before the package 100 is sealed.

In one or more embodiments, the closing and sealing of first chamber 112 and the second chamber 114 can be by the application of a heat seal, mechanical engagement, adhesive engagement, etc. In addition, one of ordinary skill in the art will appreciate that the present invention is not limited with respect to the location of the webbings, and the specific configuration illustrated and described herein. The seals can be configured and located in a number of different implementations, so long as the webbings provide the functionality of sealing off a chamber.

According to another embodiment, the invention may be practiced with an automatic high-speed blister pack system. Blister packs can be created via thermoforming or cold forming. In the case of thermoforming, a plastic film or sheet is unwound from a reel and guided through a pre-heating station on the blister line. The temperature of the pre-heating plates is such that the plastic will soften and become pliable. The warm plastic then arrives in a forming station where a large pressure forms the blister cavity into a negative mold. The mold is cooled such that the plastic becomes firm again and maintains its shape when removed from the mold.

In the case of cold forming, an aluminum based-laminate film is simply pressed into a mold by means of a stamp. The aluminum elongates and maintains the formed shape. The use of aluminum offers a complete barrier for water and oxygen.

The thermoform able backing of the medical blister pack is generally comprised of a flexible thermoform able plastic film. The film is often multi-layered. The primary component is regularly a layer of approximately 15-30% Nylon, while the remaining layers can comprise substances including, but not limited to, polyethylene. The sealant layer can comprise, among others, ethyl vinyl acetate (EVA).

In one or more embodiments, the lidding film of a medical blister pack can be made from gas impermeable material. In another embodiment, the lidding film of a medical blister pack can be made from plastic, aluminum, or medical grade papers that are permeable to gases for sterilization but are impermeable to microorganisms. Most commonly, Tyvek® is used as a lidding material for medical blister packs.

Blister packs can be sealed in a variety of ways including, but not limited to, heat-sealing and cold sealing. Lidding materials can have a heat-seal coating applied to them; the lidding is then sealed to the backing using heat, which activates the coating. Blister packs can also be sealed using a cold seal process, which uses a combination of a pressure sensitive fold-over blister card and a transparent blister; the blister is trapped between two pieces of board that are bonded together under pressure without using any heat. Additionally, blister packs can be sealed by orienting multiple layers of film properly in order to make a seal.

In one or more embodiments, the blister pack comprising a gas permeable header section and gas-impermeable section undergoes steam sterilization in an autoclave. In one or more embodiments, sterilization may also be by heat, nitrous dioxide, or a combination thereof. Following sterilization, the gas permeable section of the backing is cut and removed from the gas impermeable section by cutting along a separation line to create a gas impermeable pouch. A gas impermeable lidding material is sealed to the backing creating a gas impermeable blister pack. Because the medical device, e.g. pre-filled syringe, plastic ampoule, drug vial with rubber stopper, IV solution bag, IV solution pouches, etc. is fully enclosed in pouch consisting only of gas-impermeable film, the pouch containing the pre-filled syringe may be place in a kit that will undergo subsequent EtO sterilization without any adverse effects to the pre-filled syringe.

Blister packs are commonly used as unit-dose packaging for pharmaceutical tablets, capsules, or lozenges. The pharmaceutical product and its blister pack act together to serve as an integral unit. The blister pack protects the pharmaceutical product from outside influences that would otherwise render it useless while allowing the manufacturer of the pharmaceutical product to package it using form-fill-seal equipment. The form-fill-seal process involves creating the blister pack from rolls of flat sheet or film, filling with the pharmaceutical product, such as a drug tablet, and closing (sealing). This type of blister pack is sometimes referred to as push-through-packs because the consumer can push the good (e.g. drug tablet) through the backing. With pharmaceutical blister packs, manufacturers must be concerned with the moisture vapor transmission rate of the blister pack because many pharmaceutical products degrade and lose their efficacy through hydrolysis. Additionally, the blister pack must provide a barrier to oxygen in order to prevent degradation of the pharmaceutical product through oxidation. In one or more embodiments, the blister pack is a push-through-pack.

Blister packs can be created via thermoforming or cold forming. In the case of thermoforming, a plastic film or sheet is unwound from a reel and guided through a pre-heating station on the blister line. The temperature of the pre-heating plates is such that the plastic will soften and become pliable. The warm plastic then arrives in a forming station where a large pressure forms the blister cavity into a negative mold. The mold is cooled such that the plastic becomes firm again and maintains its shape when removed from the mold.

In the case of cold forming, an aluminum based-laminate film is simply pressed into a mold by means of a stamp. The aluminum elongates and maintains the formed shape. The use of aluminum offers a complete barrier for water and oxygen. However, cold form blister packs take longer to produce compared to thermoforming. Cold form blister packs are also not transparent, which can lead to consumers not complying with pharmaceutical therapies.

The thermoformable backing of the medical blister pack is generally comprised of a flexible thermoform able plastic film. The film is often multi-layered. The primary component is regularly a layer of approximately 15-30% Nylon, while the remaining layers can comprise substances including, but not limited to, polyethylene. The sealant layer can comprise, among others, ethyl vinyl acetate (EVA).

Blister packaging can also include the skin pack, where a paperboard or other backing material and product are covered with a thin sheet of transparent plastic. The backing generally has a heat-seal coating. The plastic film is softened by heat and draped over the product on the backing. Vacuum is sometimes used to assist in a snug fit. Immediately after forming the blister, the blister is transported to a vacuum sealing station where a vacuum is pulled and the blister is sealed shut, providing the snug fit. The plastic film bonds to the heat-seal coating on the paperboard or other backing. In one or more embodiments, the blister pack is a vacuum sealed thermoformed blister pack.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as disclosed.

What is claimed is:

1. A package container comprising:
   a package body having a top surface and a bottom surface,
   a first chamber protruding from the bottom surface of the package body having sidewalls and a closed chamber floor,
   a first cavity comprising the top surface of the body, the sidewalls of the first chamber and the closed chamber floor of the first chamber;
   a second chamber protruding from the bottom surface of the body having closed sidewalls and an at least partially open chamber floor, the top surface of the body;
   a second cavity comprising the sidewalls of the second chamber and the at least partially open chamber floor;
   a first removable webbing disposed over the top surface of the body; and,
   a second removable webbing disposed over the at least partially open chamber floor.

2. The package container of claim 1, wherein a first device is positioned within the first cavity.

3. The package container of claim 1, wherein a second device is positioned within the second cavity.

4. The package container of claim 1, wherein the first removable webbing has a peel tab.

5. The package container of claim 1, wherein the first removable webbing is peelable.

6. The package container of claim 1, wherein the second removable webbing is cut along the upper surface of the cavity.

7. The package container of claim 2, wherein the cavity of the first chamber has a length slightly larger or equal to a total length of the first device, a width slightly larger or equal to a maximum width of the first device, and a depth slightly larger or equal to a maximum depth of the first device.

8. The package container of claim 3, wherein the cavity of the second chamber has a length slightly larger or equal to the total length of the second device, a width slightly larger or equal to the maximum width of the second device and a depth slightly larger or equal to a maximum depth of the second device.

9. The package container of claim 1, wherein the second removable webbing is peelable.

10. The package container of claim 1, wherein the first removable webbing and the second removable webbing include a gas permeable section attached to a separate gas impermeable section.

11. The package container of claim 1, wherein the second removable webbing include a gas permeable section attached to a separate gas impermeable section.

12. The package container of claim 1, wherein an outer periphery of the first removable webbing includes a gas permeable section and an inner region surrounded by the outer periphery is a gas-impermeable section.

13. The package container of claim 1, wherein an outer periphery of the second removable webbing includes a gas permeable section and an inner region surrounded by the outer periphery is a gas-impermeable section.

14. The package container of claim 1, wherein the first removable webbing is gas impermeable.

15. The package container of claim 1, wherein the first removable webbing is gas permeable.

16. The package container of claim 1, wherein the second removable webbing is gas impermeable.

17. The package container of claim 1, wherein the second removable webbing is gas permeable.

* * * * *